United States Patent [19]

Brumfield

[11] 4,311,589

[45] Jan. 19, 1982

[54] TOROIDAL FLOW BLOOD REACTOR

[75] Inventor: Robert C. Brumfield, Incline Village, Nev.

[73] Assignee: Biomedics, Inc., Arlington Heights, Ill.

[21] Appl. No.: 92,053

[22] Filed: Nov. 6, 1979

[51] Int. Cl.³ .................... B01D 17/00; B01N 43/00
[52] U.S. Cl. .................... 210/177; 210/187; 210/198.1; 210/927; 422/44
[58] Field of Search .................... 210/49, 51, 78, 83, 210/84, 177, 185, 187, 198 R, DIG. 23; 366/339; 422/44; 435/2

[56] References Cited

U.S. PATENT DOCUMENTS

| | | | |
|---|---|---|---|
| 2,190,596 | 2/1940 | Dorr | 210/49 |
| 2,911,057 | 11/1959 | Green et al. | 55/16 X |
| 3,096,255 | 7/1963 | Redenbaugh | 210/177 X |
| 3,346,117 | 10/1967 | Page, Jr. | 210/304 |
| 3,422,008 | 1/1969 | McLain | 55/16 X |
| 3,730,835 | 5/1973 | Leeper et al. | 422/44 X |
| 4,028,056 | 6/1977 | Snyder et al. | 210/DIG. 23 |
| 4,061,141 | 12/1977 | Hyden et al. | 422/44 X |
| 4,181,609 | 1/1980 | Wardlaw et al. | 210/DIG. 23 |

*Primary Examiner*—Robert H. Spitzer

[57] ABSTRACT

A reactor suitable for extracorporeal treatment of blood includes a conduit defining within itself a passage of generally circular cross section and wound in a plurality of concentric helices so as to generate a transverse double toroidal secondary fluid flow in a fluid passing through the conduit. A spacer means is provided about the conduit to separate adjacent helices and permit circulation of a heat transfer fluid around each helix of the conduit.

5 Claims, 3 Drawing Figures

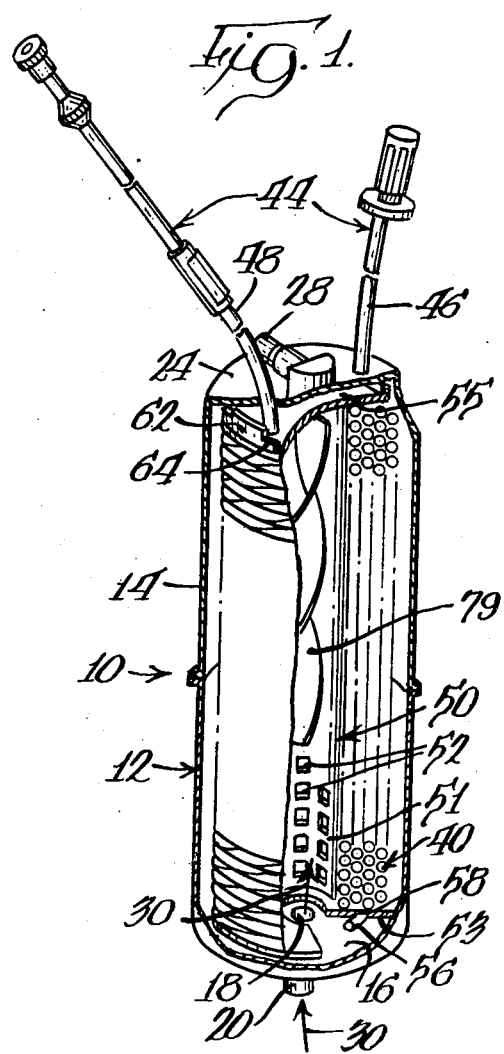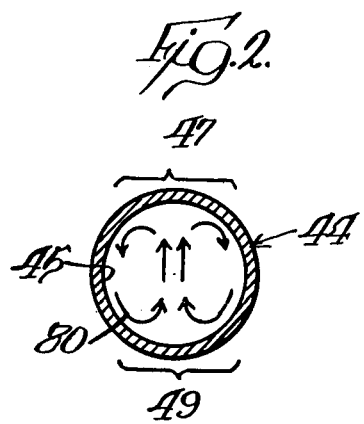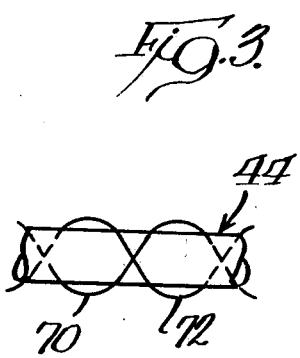

TOROIDAL FLOW BLOOD REACTOR

DESCRIPTION

TECHNICAL FIELD

This invention relates to a reactor for the extracorporeal treatment of blood.

BACKGROUND OF THE INVENTION

In the treatment of sickle cell anemia, it is desired to treat the human blood extracorporeally by contacting the blood with a cyanate source such as sodium cyanate (NaNCO) to effect the carbamylation of the sickle cell hemoglobin.

Where the reaction of a cyanate with the blood is to be effected extracorporeally, a number of factors must be considered. First, physical damage to the blood, and especially to the red blood cells, must be avoided. Therefore, it would be desirable to provide a suitable hemo-reactor for treating the blood in which damaging turbulent flow within the reactor is avoided or at least minimized.

Second, sufficient mixing of the cyanate with the blood must nevertheless be achieved in order to effect efficient carbamylation of the sickle cell hemoglobin in a relatively short period of time. Consequently, it would be desirable to provide a reactor in which the cyanate and blood are effectively and efficiently mixed without damaging the red blood cells.

Third, reaction of the cyanate with blood constituents is most desirably carried out at an elevated but controlled temperature. Thus, it would be desirable to provide a reactor in which the temperature of the reacting components, such as the blood constituents and the cyanate, is raised to, and maintained at, a predetermined value during the reaction. Further, in order to provide efficient heat transfer and to avoid undesirable temperature gradients in the reacting admixture, it would be desirable to provide a reactor exhibiting suitable heat transfer characteristics.

Fourth, it would be desirable to provide a reactor which is relatively compact in order to facilitate its use with other equipment and so as to reduce the amount of space required in any medical facility making use of such a reactor.

SUMMARY OF THE INVENTION

A reactor of the present invention is especially adapted for treating a body fluid such as blood with one or more therapeutic agents such as a cyanate, nitrogen mustard, methotrexate or the like. The assembly provides for substantially plug flow therethrough for a first fluid stream (the fluid to be treated) with a simultaneous secondary toroidal flow which mixes components present in the first fluid stream and situates the first fluid stream in an improved thermal energy exchange relationship with a second fluid stream which serves as a heat transfer medium so as to attain and maintain a predetermined first fluid temperature.

The reactor embodying the present invention provides an extracorporeal flow path for the first fluid (e.g., blood and a therapeutic agent) with a first in-first out unit volume flow sequence and with in-line mixing. At the same time the extracorporeal flow path can be submerged in a second flowing fluid for effecting a thermal energy exchange between the fluids so as to rapidly attain and maintain a predetermined first fluid temperature.

The reactor assembly includes a conduit defining within itself a winding passage of generally circular cross section for conducting the first fluid in a generally first in-first out linear flow sequence therethrough. The conduit, such as a thermoplastic tubing, is wound or coiled about a longitudinal axis in a plurality of concentric helics so that a centrifugally-induced, transverse double toroidal secondary flow is generated within the passage to effect mass transport and mixing of the components in the first fluid between the center of the passage and the periphery of the passage. A degree of chemical reaction that closely approximates that of a plug-flow chemical reactor is attained as well. Such a high degree of reaction translates directly into shortened treatment time.

Spacer means, such as one or more small diameter filaments spirally wound around the tubing, is provided to separate at least radially adjacent helics and to permit circulation of the second fluid around the conduit in each helix, thereby promoting effective heat transfer between the first and second fluids.

The novel combination of elements in accordance with the present invention yields desirable and beneficial results—results which provide a substantial improvement over the prior art.

Numerous other advantages and features of the present invention will become readily apparent from the following detailed description of the invention, from the claims and from the accompanying drawings.

BRIEF DESCRIPTION OF THE DRAWINGS

In the accompanying drawings forming part of the specification and in which like numerals are employed to designate like parts throughout the same, FIG. 1 is a perspective view of the apparatus of the present invention, partially cut away to illustrate the interior structure;

FIG. 2 is a cross-sectional view of the tubing forming a part of the apparatus; and FIG. 3 is a diagrammatic view of a portion of the tubing showing a pair of spiral wound spacer filaments on the exterior of the tubing.

DESCRIPTION OF PREFERRED EMBODIMENTS

This invention may be used in many different forms. The invention is not intended to be limited to the embodiments illustrated, and the scope of the invention will be pointed out in the appended claims.

The precise shapes and sizes of the components herein described are not essential to the invention unless otherwise indicated.

For ease of description, the apparatus of this invention will be illustrated and described in a particular orientation, i.e., as shown in the accompanying drawings. It will be understood, however, that the apparatus of this invention may be manufactured, stored, transported and sold, as well as used, in an orientation other than that illustrated.

For optimum performance of the reactor embodying the present invention the following design criteria are significant to provide substantially plug flow of fluid stream to be treated, e.g., blood in admixture with a chemotherapeutic agent. The flow dispersion in this fluid stream preferably should be about 0.02 or lower, more preferably about 0.01. Flow dispersion in a liquid stream is given by the expression $$\text{flow dispersion} = Du/L$$

where D is solute diffusivity in cm$^2$/minute, u is linear flow velocity in cm/minute, and L is length of flow path in cm.

The reactor of the present invention minimizes flow dispersion by providing a coiled conduit for the fluid stream to be treated, i.e., the first fluid stream, and thus inducing a substantially toroidal secondary flow therewithin. Intensity of the induced secondary flow is proportional to the square root of the Dean Number which can be calculated from the expression $$\text{Dean No.} = Re(r_t/R_c)^{\frac{1}{2}}$$

where Re is Reynolds Number, $r_t$ is the inside radius of the conduit, and $R_c$ is the inside radius of the conduit coil. Thus, the greater the Dean Number the greater is the intensity of the induced secondary flow, and the closer the fluid flow within the conduit approximates plug flow. For a reactor embodying the present invention the ratio of $r_t$ to $R_c$ preferably is about 0.025 to about 0.1, and more preferably about 0.04 to about 0.08.

The pressure drop across the conduit is also a significant factor and preferably should not exceed about 100 mm of mercury at the operational fluid flow rates with the Reynolds Number in the laminar flow region, and preferably at a value of less than about 200. In the case of blood chemotherapy, the fluid shear rate at the conduit wall should be greater than about 50 sec$^{-1}$ in order to avoid, or at least minimize, the Rouleaux effect. More preferably, for blood chemotherapy the fluid shear rate at the conduit will should be greater than about 75 sec$^{-1}$.

Heat transfer efficiency is also important, particularly when the fluid to be treated is blood. For the latter, it is desirable that the average temperature within the blood-carrying conduit be maintained at a level as high as possible commensurate with limitations imposed by hemolysis and red blood cell survival rates in order to minimize necessary residence time within the reactor and thus the total time of treatment needed. To this end, it has been found that the blood temperature can be maintained as high as about 43° C. without adversely affecting the blood hematologically, and the effective heat transfer area of the conduit as well as the flow rate of the heat transfer medium, i.e., the second fluid stream, through the reactor should be selected accordingly.

Referring now to FIG. 1, the elements of the hemo-reactor 10 embodying the present invention are illustrated. Reactor 10 includes a casing or tank 12 having a generally cylindrical shell 14, which may be formed as two longitudinally aligned halves bonded together. If the hemo-reactor is to be of the reusable type, shell 14 can be made of stainless steel or similar material. For disposable hemo-reactors, on the other hand, shell 14 can be made of thermoplastic or thermosetting polymeric materials that are generally acceptable for use in medical equipment. The tank 12 includes a generally circular first end wall 16 defining an inlet orifice 18 for a heat transfer medium, i.e., a heating fluid or cooling fluid. Fluid inlet nozzle 20 projects outwardly from end wall 16. The tank 12 also includes a generally cylindrical second end wall 24 defining an outlet orifice (not visible in FIG. 1) which includes an integral outlet nozzle structure 28. In FIG. 1, the heating or cooling fluid entering through the inlet nozzle 20 flows upwardly through the tank 12 as indicated by arrows 30 and eventually exits through the discharge nozzle 28.

The fluid to be treated (such as blood and one or more of various therapeutic agents), flows in a convoluted conduit assembly 40 mounted within the tank 12 in a spaced relationship from the sidewalls of tank 12. In operation, the tank 12 is filled with the flowing heating or cooling fluid so that the assembly 40 is entirely submerged therewithin.

The assembly 40 includes a convoluted conduit 44 having an inlet portion 46 and an outlet portion 48 passing through the end wall 24. The end wall 24 is sealed around the inlet and outlet portions 46 and 48 of conduit 44 to prevent out leakage of the heating or cooling fluid. Although the inlet and outlet portions 46 and 48 of conduit 44 are illustrated as passing through the same end wall 24 of the tank, it is to be realized that both inlet and outlet portions 48 could be arranged to pass through the other end wall 16 of the tank. Also, just one of the tubing portions, 46 or 48, could be arranged to pass through the end wall 16 with the remaining portion passing through end wall 24.

The conduit 44 may be made from any suitable material, such as polyvinyl chloride tubing typically having an OD of about 0.281 inch and an ID of about 0.165 to about 0.188 inch. In the case of blood treatment, the material, of course, should be non-thrombogenic. Inside of the tank 12, the tubing 44 is arranged in a plurality of concentric helices about a longitudinal axis which, in the preferred embodiment illustrated, is coincident with the longitudinal axis of the generally cylindrical tank shell 14. The resulting coiled structure is one in which a plurality of substantially co-axial helices are formed around the longitudinal axis of the tank 12 in layers of increasingly larger diameter.

In a preferred embodiment, the conduit 44 is wound around, and at least in part supported by, a spool member 50 comprising a generally cylindrical, foraminous core 51 and core end flanges 53 and 55. In yet another preferred embodiment, the core can be solid, defining an annular space within which the convoluted conduit is situated and through which annular space the heat transfer medium can be circulated. If a solid core is utilized, core end flanges are, of course, omitted and the incoming heat transfer medium is distributed over the convoluted conduit by means of an appropriate header. The core may be made of any suitable material, such as polypropylene, and may be solid or foraminous, e.g., provided with a plurality of perforations 52 through which the heating or cooling fluid can be distributed.

As shown in FIG. 1, foraminous core 51 is provided with end flanges 53 and 55 substantially parallel to one another and oriented in planes parallel to the plane defined by the end wall 16. To prevent leakage of the heating or cooling fluid between the flange 53 and the interior surface of the end wall 16, an O-ring 56 is positioned in a suitable receiving groove 58 provided in the flange 53. Preferably, the core 51 has an internal diameter equal to or greater than the tank inlet 18 defined within tank end wall 16 on the interior of the core 51 so that the heating or cooling fluid flows from the interior of the core radially outwardly through the core. The inlet and outlet portions of tubing 44 preferably pass through the core end flange 55 which, in turn, may be provided with suitable bores or apertures for receiving the tubing.

Core end flange 55 also functions as a baffle plate defining first and second generally cylindrical, axially aligned, internal chambers within the tank 12. The first chamber contains the helical configurations of conduit 44 and the second chamber is located adjacent the outlet end of tank 12 in communication with the discharge nozzle 28.

The core end flange 55 terminates radially short of the cylindrical shell 14 of the tank 12 to provide communication around the baffle plate between the first and second chambers so that a portion of the heating or cooling fluid flowing into the tank through the inlet orifice 18 can eventually flow around the core end flange 55 and out the tank discharge nozzle 28. The core end flange 55 and foraminous core 51 are retained in their proper axial positions within the tank 12 by means of a spacer ring 62 which is positioned between the inside surface of tank end wall 24 and the core end flange 55 and which may be secured to, or formed integrally with, the core end flange 55. The spacer ring 62 has appropriate cut outs or notches 64 to permit passage of the heating or cooling fluid around the core end flange 55.

By forming the conduit 44 into the plurality of helices illustrated in FIG. 1, improved mixing and radial mass transport of non-turbulent flow conditions is obtained. Specifically, in FIG. 2 secondary flow patterns within the cross section of the conduit 44 are illustrated. The conduit 44 is seen to have a generally circular internal flow passageway 45. The outer or convex region of the helix segment formed by the conduit is designated by 47 and the inside or concave side of the helix segment is designated by 49. Owing to the centrifugally-induced forces acting on the gross or primary fluid flow in the conduit, a radial mass transport in the form of a double toroidal secondary flow is thus produced generally transverse to the gross fluid flow in a pattern generally illustrated by the arrows 80. This secondary flow, imposed upon the primary flow, aids in heat transfer and mixing of the fluid constituents between the center of the passageway 45 and the periphery of the passageway 45 within the conduit 44.

Though not illustrated, additional mixing of the treated fluid can be induced by providing an appropriate twisted, elongated planar member within the passageway 45, such as a twisted ribbon of metal or plastic.

By appropriately choosing the diameter of the conduit and the material of conduit construction, the reactor 10 can be operated at a desired flow rate within the conduit so that the flow is substantially non-turbulent. With some fluids, such as with whole blood, avoidance of turbulent flow is necessary to prevent damage to the blood components.

Preferably, the helical configuration of the tubing 44 is arranged to permit the heating or cooling fluid to flow around substantially all of the exterior surface of the tubing within the tank 12. Accordingly, it is desirable to effect a relatively uniform heat transfer capability per unit tubing length throughout the configuration of helices within the tank 12. Thus, it is desired to avoid a configuration in which substantial portions of the surface of the tubing 44 are not contacted by flowing heating or cooling fluid. To this end, a substantially continuous spacer structure is provided for at least radially separating adjacent helices so as to permit circulation of the heating or cooling fluid around the tube in each helix. Preferably, as best illustrated in FIG. 3, the tubing 44 includes a ridge member or members, such as a plurality of filaments, e.g., generally cylindrical filaments 70 and 72, extending in overlapping spiral loci around the surface of the tubing. The filaments 70 and 72 are preferably each a solid, monofilament of a suitable material, such as polyethylene, polypropylene, or nylon of a suitable diameter.

For example, it has been found that with tubing 44 having an outside diameter of 0.281 inch, a polyethylene or nylon monofilament having a diameter of 0.047 inch provides a satisfactory spacing between adjacent portions of the tubing 44 when the tubing 44 is arranged in a plurality of helices as illustrated in FIG. 1. Preferably, the sizes of the filaments 70 and 72 and of the tubing 44, as well as the pitch of the winding of the filaments 70 and 72, are chosen such that, for a particular volumetric flow rate of the heating or cooling fluid through the tank or casing 12, the Reynolds Number that is characteristic of the heating or cooling fluid flow is well within the turbulent region. With such a design, the heating or cooling fluid passing radially outwardly from the center of the shell 14 and through the configuration of helices can have a significant effect on the temperature of the fluid flowing in the tubing 44 within a relatively small percentage of the total tubing length within the tank 12.

As an example of an effective hemo-reactor constructed in accordance with the teachings of the present invention, the reactor illustrated in FIG. 1 can have an overall length of about 13 inches and an outside diameter of about 4½ inches. Shell 14 can be molded from DYLARK 232, a styrene-maleic anhydride copolymer as two halves commercially available from ARCO Polymers, Inc., which are bonded together using methylene chloride. Other suitable materials of construction for shell 14 can be polyvinyl chloride, usually bonded together using cyclohexane, polyurethane, usually bonded together using tetrahydrofuran, and the like. Approximately 80–90 feet of polyvinyl chloride tubing, having an inside diameter of 0.165–0.188 inch to give a net volume of about 400 cc, and an outside diameter of 0.281 inches, is wrapped on its exterior with a pair of 0.047 inch diameter polypropylene monofilaments co-wound in overlapping spiral loci as shown in FIG. 3 and with a pitch of about 1½ inches. The filament-wrapped tubing is wound about the core 50 to form four concentric helices about the longitudinal axis of the shell 12. The diameter of the innermost helix, as measured to the center line of the tubing 44, is about 2 inches and the diameter of the outermost helix, similarly measured to the center line of the tubing 44, is about 4 inches. With this construction, the pressure drop through the tubing 44, as measured across the inlet and outlet ends 46 an 48 respectively, is less than 18 mm of mercury at a water flow rate of 40 ml/mm.

To further enhance heat transfer through the entire length of tubing 44, an axial baffle 79, such as a twisted strip of about 1/16-inch thick thermoplastic material or stainless steel may be disposed within the interior of the cylindrical core 51, for example, depending from core end flange 55, for deflecting the entering heating or cooling fluid radially outwardly away from the longitudinal axis of the tank 12 and through the spaced helices of tubing 44.

Although the separating or spacer ridge members 70 and 72 are illustrated as being formed from small diameter filaments co-wound in spiral loci about the tubing 44, it is to be realized that the spacer structure may be provided integrally with the wall of the tubing 44, as with one or more outwardly projecting continuous ridges to substantially duplicate the structure of one or both of the filaments 70 and 72.

Of course, other forms of spacing means may be used, either continuous or intermittent with respect to the surface of the tube 44. As another alternative, the tubing 44 could be co-wound in its helical configuration with a strip of open-pore foam to provide a ventilated matrix spacer. Also, spacer collars, such as rings of foam, could be circumferentially disposed about each helix, at axially spaced locations within the tank to effect a radial separation of adjacent helices.

In the embodiment illustrated in FIG. 1, the tubing 44 is closely wound in each helix so that the spiral monofilaments 70 and 72 necessarily provide axial separation of adjacent turns within the same helix as well as radial separation of adjacent concentric helices. It is to be realized that the axial separation of adjacent turns within the same helix could be maintained without the use of filaments. For example, the helices may be wound with a greater pitch to provide a relatively greater axial separation spacing between adjacent turns. The axial spacing could be maintained by co-winding the tubing 44 into the helix configuration with a coextensive spring member, such as a coiled spring, which has the desired spacing. With such relatively larger turn spacings, the outer concentric helices may tend to fill in the spacings of the inner helices. To avoid this, a generally cylindrical, foraminous screen can be placed over each completed helix. The screen could be not unlike the foraminous core member 51 illustrated in FIG. 1, although the thickness of such a screen could be relatively thin since it need not serve to support the helix assembly, but merely radially separate adjacent helices. With the tubing co-wound with a spring member, some amount of radial and lateral separation of the tubing surfaces will be provided—even without the cylindrical screens being placed between adjacent, concentric helices.

As another example, a toroidal secondary flow blood reactor structure comprises a helical blood conduit of at least 150 radians of convolution of average turn radius of curvature not exceeding six centimeters immersed in a heat transfer bath of 35° to 45° C. During blood treatment wherein a mixture of primate blood and a therapy agent flow through the conduit, the mixture is maintained at about 43° C.

From the foregoing, it will be observed that numerous variations and modifications may be effected without departing from the spirit and scope of the novel concept of the invention. It is to be understood that, unless expressly stated, no limitation with respect to the specific apparatus illustrated herein is intended or should be inferred. It is, of course, intended to cover by the appened claims all such modifications as fall within the scope of the claims.

I claim:

1. A core assembly for a reactor suitable for extracorporeal treatment of blood, and comprising:
    a conduit defining within itself a passage of generally circular cross section for conducting an introduced fluid in a generally first in-first out flow sequence, said conduit being wound about a longitudinal axis in a plurality of concentric helices generating a centrifugally-induced, transverse double torodial secondary fluid flow within said passage to effect radial mass transport therewithin and mixing between the center and the periphery of said passage; and
    spacer means at least radially separating adjacent helices for permitting circulation of a heat transfer fluid around said conduit in each helix;
    said spacer means including a ridge member extending in a spiral locus about said conduit.

2. The assembly in accordance with claim 1 in which said spacer means also includes means axially separating adjacent turns of said conduit in each said helix.

3. The assembly in accordance with claim 1 in which said conduit is tubular and has a wall with an annular cross-section.

4. The assembly in accordance with claim 1 in which said ridge member is a generally cylindrical filament wound around the exterior of said conduit.

5. A linear reactor for effecting first in-first out, in-line flow sequence for a first fluid stream and for effecting a thermal energy exchange between said first fluid stream and a second fluid stream to attain and maintain a predetermined first fluid temperature, such as in the extracorporeal treatment of blood, said reactor comprising:
    a tank means for circulating said second fluid and having an inlet for said second fluid and an outlet for said second fluid;
    a convoluted conduit defining within itself a passage having a generally circular cross section for conducting said first fluid in a generally first in-first out flow sequence, said conduit having inlet and outlet portions passing through said tank for accommodating the flow of said first fluid, said conduit being arranged in a plurality of helices generally concentric about a longitudinal axis and generating a centrifugally-induced, transverse double toroidal secondary flow within said passage;
    spacer means at least radially separating adjacent helices for permitting circulation of said second fluid around said conduit in each said helix to promote heat transfer between said first and second fluids; and
    a baffle means disposed interior of said conduit helices for deflecting a portion of said second fluid flow entering said shell through said inlet away from said longitudinal axis and through said conduit helices.

* * * * *

Notice of Adverse Decision in Interference

In Interference No. 101,098, involving Patent No. 4,311,589, R. Brumfield, TOROIDAL FLOW BLOOD REACTOR, final judgment adverse to patentee was rendered Mar. 14, 1985, as to claims 1–5.

[*Official Gazette April 30, 1985.*]